(12) United States Patent
Ota et al.

(10) Patent No.: US 8,853,649 B2
(45) Date of Patent: Oct. 7, 2014

(54) FLUORESCENCE SENSOR

(71) Applicant: Terumo Kabushiki Kaisha, Tokyo (JP)

(72) Inventors: Ryo Ota, Nagano (JP); Etsuro Shimizu, Shiojiri (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/869,213

(22) Filed: Apr. 24, 2013

(65) Prior Publication Data

US 2013/0234042 A1 Sep. 12, 2013

Related U.S. Application Data

(63) Continuation of application No. PCT/JP2011/074164, filed on Oct. 20, 2011.

(30) Foreign Application Priority Data

Oct. 25, 2010 (JP) ................................. 2010-238802

(51) Int. Cl.
 G01J 1/58 (2006.01)
 G01N 21/64 (2006.01)
 G01N 21/77 (2006.01)
(52) U.S. Cl.
 CPC ............... G01N 21/64 (2013.01); G01N 21/77 (2013.01); G01N 2021/7786 (2013.01)
 USPC .................................... 250/458.1; 250/459.1
(58) Field of Classification Search
 CPC .................................................... G01N 21/64
 USPC .......................................... 250/458.1, 459.1
 See application file for complete search history.

(56) References Cited

U.S. PATENT DOCUMENTS

| 4,755,667 | A | | 7/1988 | Marsoner et al. |
| 5,039,490 | A | | 8/1991 | Marsoner et al. |
| 5,157,262 | A | | 10/1992 | Marsoner et al. |
| 5,399,868 | A | * | 3/1995 | Jones et al. ................ 250/484.2 |
| 5,517,313 | A | | 5/1996 | Colvin, Jr. |
| 5,894,351 | A | | 4/1999 | Colvin, Jr. |
| 5,917,605 | A | | 6/1999 | Colvin, Jr. |
| 2004/0161853 | A1 | | 8/2004 | Yang et al. |
| 2005/0157301 | A1 | | 7/2005 | Chediak et al. |

FOREIGN PATENT DOCUMENTS

| EP | 0 244-394 A2 | 11/1987 |
| EP | 0 263 805 A2 | 4/1988 |

(Continued)

OTHER PUBLICATIONS

International Search Report dated Dec. 6, 2011 issued in PCT/JP2011/074164.

*Primary Examiner* — David Porta
*Assistant Examiner* — Abra Fein
(74) *Attorney, Agent, or Firm* — Scully, Scott, Murphy & Presser, P.C.

(57) ABSTRACT

A fluorescence sensor includes a detection substrate section, on a first principal plane of which a concave portion having a bottom surface parallel to the first principal plane is present and, on a side surface of the concave portion of which a PD element configured to receive fluorescent light and output a detection signal is formed, an LED element disposed on the bottom surface of the concave portion of the detection substrate section and configured to generate excitation light, and an indicator layer disposed on an inside of the concave portion on the LED element and configured to generate the fluorescent light corresponding to the excitation light and an analyte amount.

17 Claims, 9 Drawing Sheets

(56) References Cited

FOREIGN PATENT DOCUMENTS

| EP | 1 880 664 A2 | 1/2008 |
| JP | 62-261036 A | 11/1987 |
| JP | 63-98548 A | 4/1988 |
| JP | 11-500825 A | 1/1999 |
| JP | 2001-525930 A | 12/2001 |
| JP | 2002-502495 A | 1/2002 |
| WO | WO 96/26429 A | 8/1996 |
| WO | WO 98/52023 A1 | 11/1998 |
| WO | WO 98/52024 A1 | 11/1998 |
| WO | WO 2004/071291 A2 | 8/2004 |

* cited by examiner

PRIOR ART

FIG.7A FIG.7B
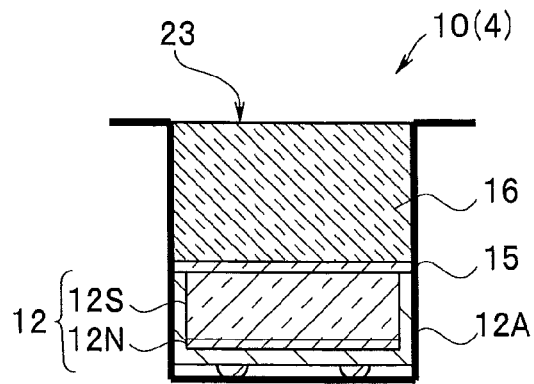
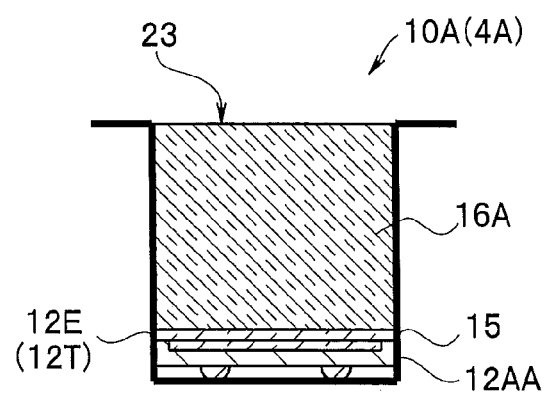
FIG.8
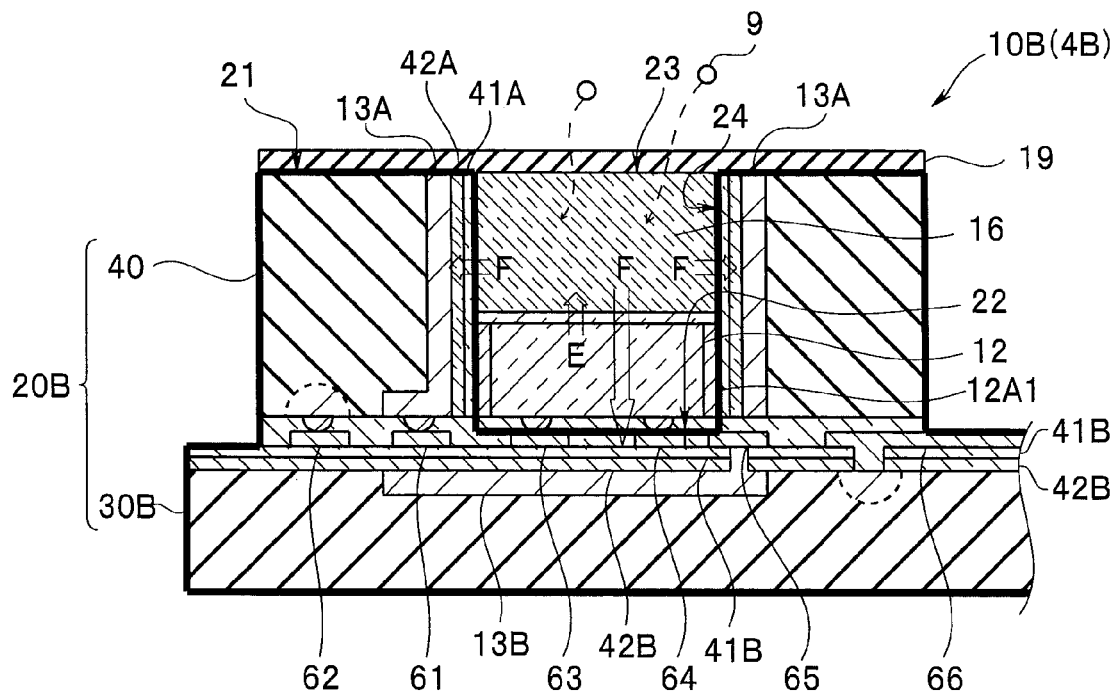

US 8,853,649 B2

FLUORESCENCE SENSOR

CROSS REFERENCE TO RELATED APPLICATION

This application is a continuation application of PCT/JP2011/074164 filed on Oct. 20, 2011 and claims benefit of Japanese Application No. 2010-238802 filed in Japan on Oct. 25, 2010, the entire contents of which are incorporated herein by this reference.

BACKGROUND OF THE INVENTION

1. Field of the Invention

The present invention relates to a fluorescence sensor for measuring a concentration of an analyte and, more particularly, to a fluorescence sensor, which is a micro-fluorescence spectrophotometer, manufactured using a semiconductor manufacturing technique and an MEMS technique.

2. Description of the Related Art

Various analyzers for checking presence of an analyte, i.e., a substance to be measured in liquid or measuring a concentration of the analyte have been developed. For example, there is a known fluorescence spectrophotometer for injecting a fluorescent pigment, which changes in characteristics because of the presence of an analyte and generates fluorescent light, and a solution to be measured including the analyte into a transparent container having a fixed capacity and irradiating an excitation light E to measure fluorescent light intensity from the fluorescent pigment to thereby measure the concentration of the analyte.

A small fluorescence spectrophotometer includes a photodetector and an indicator layer containing a fluorescent pigment. When the excitation light E from a light source is irradiated on the indicator layer into which the analyte in the solution to be measured can penetrate, the fluorescent pigment in the indicator layer generates fluorescent light with a light amount corresponding to the analyte concentration in the solution to be measured. The photodetector receives the fluorescent light. The photodetector is a photoelectric conversion element. The photodetector outputs an electric signal corresponding to the light amount of the received fluorescent light. The analyte concentration in the solution to be measured is measured from the electric signal.

In recent years, in order to measure an analyte in a micro-volume sample, a micro-fluorescence spectrophotometer manufactured using the semiconductor manufacturing technique and the MEMS technique has been proposed. The micro-fluorescence spectrophotometer is hereinafter referred to as "fluorescence sensor".

For example, a fluorescence sensor 110 shown in FIGS. 1 and 2 is disclosed in U.S. Pat. No. 5,039,490. The fluorescence sensor 110 is configured by a transparent supporting substrate 101 through which excitation E can be transmitted, an optical tabular section 105 including a photoelectric conversion element section 103 configured to convert fluorescent light into an electric signal and a light-condensing function section 105A configured to condense the excitation light E, an indicator layer 106 configured to interact with an analyte 9 to thereby generate fluorescent light through incidence of the excitation light E, and a cover layer 109.

The photoelectric conversion element section 103 is, for example, a photoelectric conversion element formed on a substrate 103A made of silicon. The substrate 103A does not transmit the excitation light E. Therefore, the fluorescence sensor 110 includes, around the photoelectric conversion element section 103, an air gap region 120 through which the excitation light E can be transmitted.

That is, only the excitation light E transmitted through the air gap region 120 and entered the optical tabular section 105 is condensed to the vicinity of an upper part of the photoelectric conversion element section 103 in the indicator layer 106 by the action of the optical tabular section 105. Fluorescent light F is generated by interaction of condensed excitation light E2 and the analyte 9 penetrating into an inside of the indicator layer 106. A part of the generated fluorescent light F enters the photoelectric conversion element section 103. A signal of an electric current, a voltage, or the like proportional to fluorescent light intensity, i.e., the concentration of the analyte 9 is generated in the photoelectric conversion element section 103. Note that the excitation light E does not enter the photoelectric conversion element section 103 by the action of a filter (not shown in the figure) that covers the photoelectric conversion element section 103.

As explained above, in the fluorescence sensor 110, on the transparent supporting substrate 101, a photodiode which is the photoelectric conversion element section 103 is formed on the substrate 103A in which the air gap region 120, which is a passage of the excitation light E, is secured. The optical tabular section 105 and the indicator layer 106 are laminated on an upper side of the substrate 103A.

SUMMARY OF THE INVENTION

A fluorescence sensor according to an aspect of the present invention includes: a detection substrate section, on a first principal plane of which a concave portion having a bottom surface parallel to the first principal plane is present and, in at least a part of a side surface of the concave portion of which a photoelectric conversion element configured to receive fluorescent light and output a detection signal is formed; a light-emitting element disposed on the bottom surface of the concave portion of the detection substrate section and configured to generate excitation light; and an indicator layer disposed on an inside of the concave portion on an upper side of the light-emitting element and configured to generate the fluorescent light corresponding to the excitation light and an analyte amount.

BRIEF DESCRIPTION OF THE DRAWINGS

FIG. 7A is a schematic diagram showing a sectional structure of the fluorescence sensor according to the first embodiment;

FIG. 7B is a schematic diagram showing a sectional structure of a fluorescence sensor according to a modification of the first embodiment;

FIG. 8 is a schematic diagram showing a sectional structure of a fluorescence sensor according to a second embodiment;

DETAILED DESCRIPTION OF THE PREFERRED EMBODIMENT

First Embodiment

A fluorescence sensor 10 according to a first embodiment of the present invention is explained below.

Figure 1:
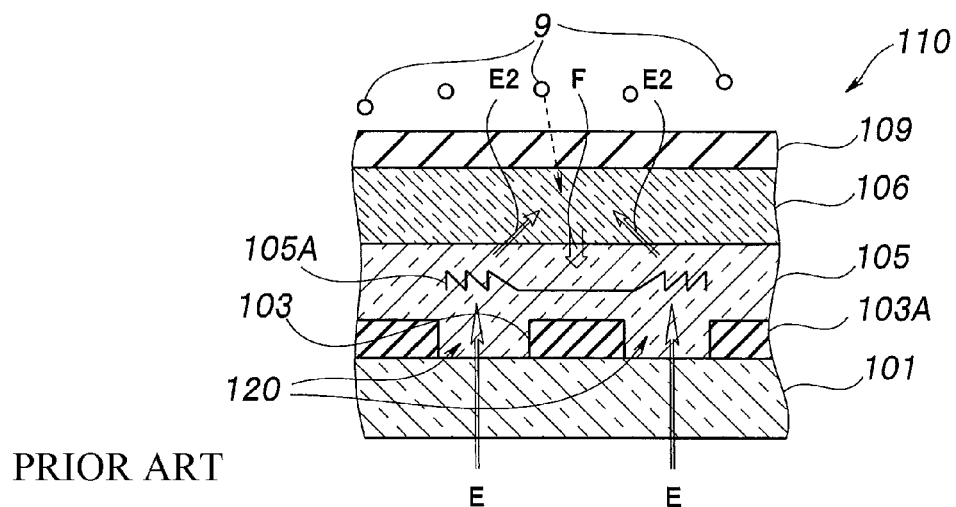
FIG. 1 is an explanatory diagram showing a sectional structure of a publicly-known fluorescence sensor.
Figure 2:
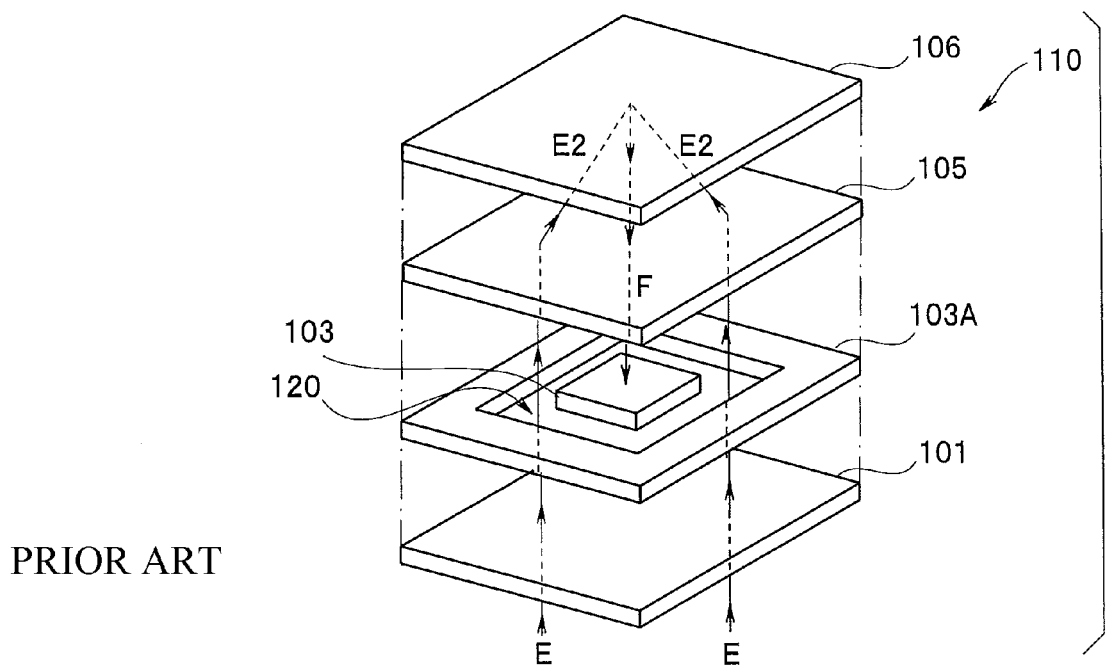
FIG. 2 is an exploded view for explaining the structure of the publicly-known fluorescence sensor.
Figure 3:
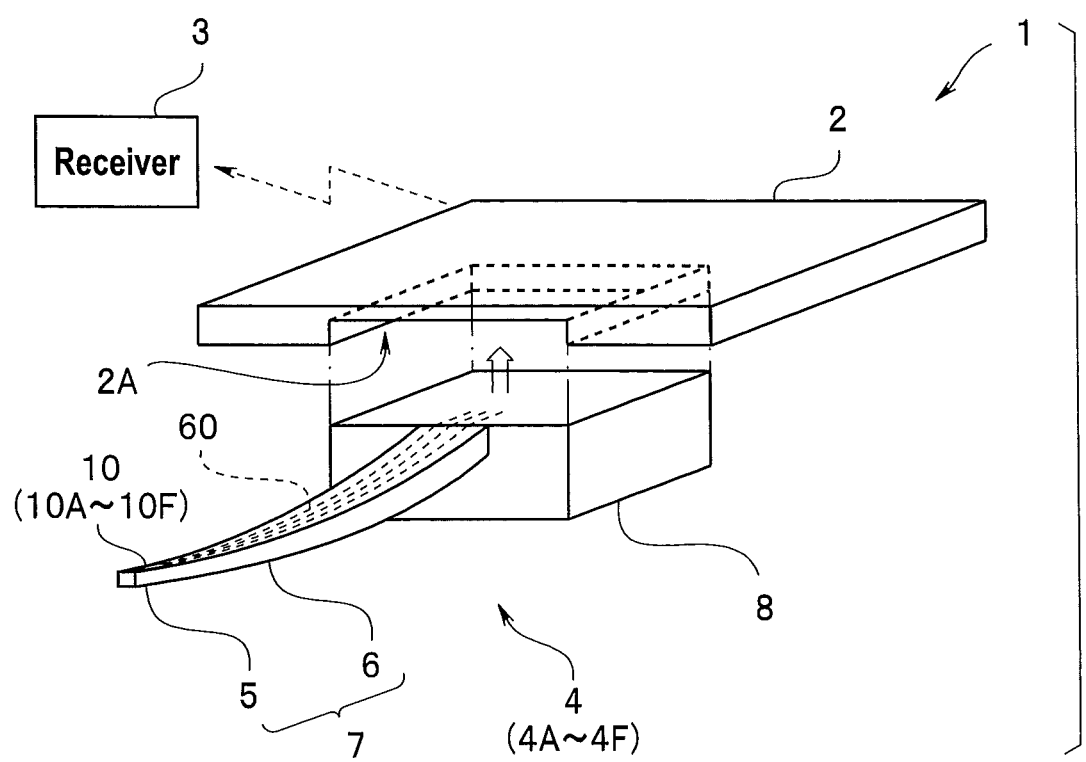
FIG. 3 is an explanatory diagram for explaining a sensor system including a fluorescence sensor according to a first embodiment.

As shown in FIG. 3, a needle-type fluorescence sensor 4 including the fluorescence sensor 10 configures a sensor system 1 in conjunction with a main body section 2 and a receiver 3.

That is, the sensor system 1 includes the needle-type fluorescence sensor 4, the main body section 2, and the receiver 3 that receives and stores a signal from the main body section 2. Transmission and reception of a signal between the main body section 2 and the receiver 3 is performed by radio or by wire.

The needle-type fluorescence sensor 4 includes a needle section 7 including a needle distal end portion 5, which includes the fluorescence sensor 10 as a main functional section, and an elongated needle main body portion 6, and a connector section 8 integrated with a rear end portion of the needle main body portion 6. The needle distal end portion 5, the needle main body portion 6, and the connector section 8 may be integrally formed by the same material.

The connector section 8 detachably fits with a fitting section 2A of the main body section 2. The connector section 8 mechanically fits with the fitting section 2A of the main body section 2, whereby a plurality of wires 60 extended from the fluorescence sensor 10 of the needle-type fluorescence sensor 4 are electrically connected to the main body section 2. In the following explanation, the plurality of wires 60 are respectively indicated by wires 61 (to 68).

Although not shown in the figure, the main body section 2 includes a computing section configured to process a detection signal from the fluorescence sensor 10, a radio antenna for transmitting and receiving a radio signal between the main body section 2 and the receiver 3, and a battery and the like. When wired transmission and reception is performed between the main body section 2 and the receiver 3, the main body section 2 includes a signal line instead of the radio antenna.

The fluorescence sensor 10 is a disposable section that is discarded after use to prevent infection. However, the main body section 2 and the receiver 3 are reusable sections that are repeatedly reused. Note that, when the main body section 2 includes a memory section having enough capacity, the receiver 3 is unnecessary.

In a state in which the needle-type fluorescence sensor 4 is fit with the main body section 2, a subject himself/herself stabs the needle-type fluorescence sensor 4 from the body surface. The needle distal end portion 5 is retained in the body. For example, the needle-type fluorescence sensor 4 continuously measures glucose concentration in body fluid and stores the glucose concentration in a memory of the receiver 3. That is, the fluorescence sensor 10 according to the present embodiment is a sensor of a short-term subcutaneous retaining type that is continuously used for about one week.

Figure 4:
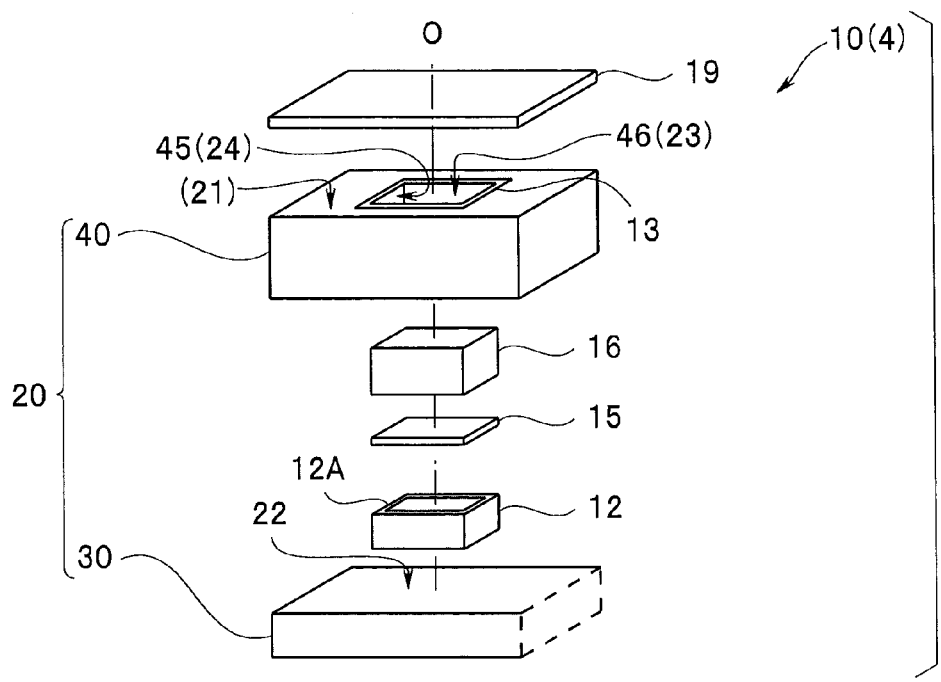
FIG. 4 is an exploded view for explaining the structure of the fluorescence sensor according to the first embodiment.
Figure 5:
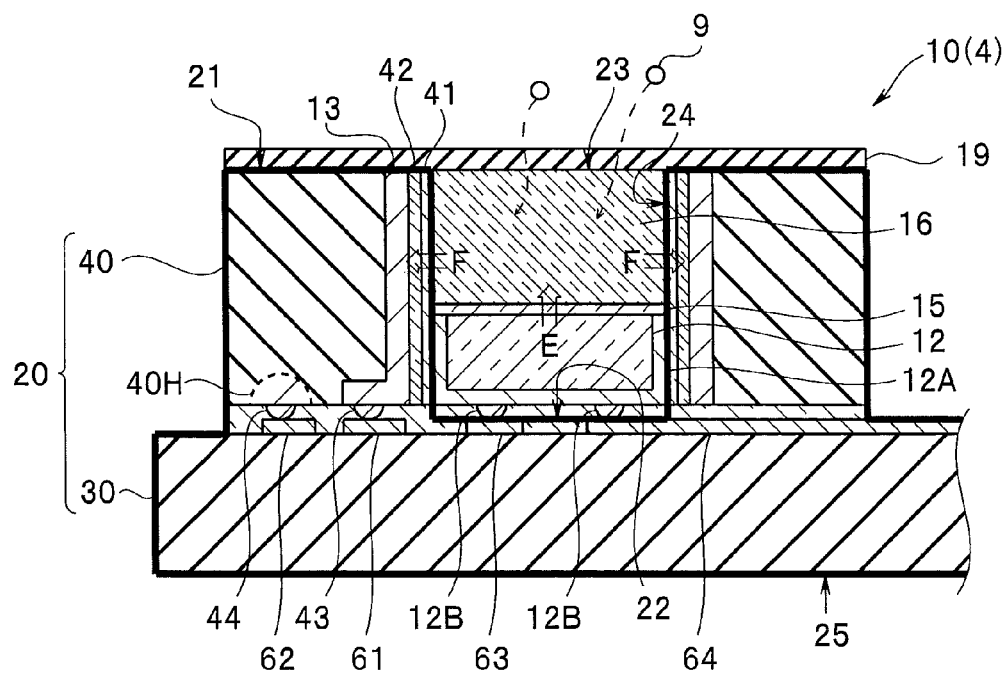
FIG. 5 is a schematic diagram showing a sectional structure of the fluorescence sensor according to the first embodiment.

As shown in FIGS. 4 and 5, the fluorescence sensor 10, which is a main functional section of the needle-type fluorescence sensor 4, includes a detection substrate section 20, a light emitting diode (hereinafter also referred to as "LED") element 12, which is a light-emitting element that generates the excitation light E, a transparent resin layer 15, an indicator layer 16 that generates the fluorescent light F corresponding to the excitation light E and an analyte amount, and a light blocking layer 19.

The detection substrate section 20 is manufactured by bonding a wiring substrate 30 and a frame-like substrate 40 in which a through-hole 46 is formed. Therefore, in the detection substrate section 20, on a first principal plane 21, a concave portion 23 having a bottom surface 22 parallel to the first principal plane 21 is present. That is, a surface of the wiring substrate 30 is the bottom surface 22 of the concave portion 23. A wall surface 45 of the through-hole 46 of the frame-like substrate 40 is a side surface 24 of the concave portion 23. Note that insulation layers are formed as appropriate on, for example, surfaces of the detection substrate section 20 made of an N-type semiconductor, i.e., the wiring substrate 30 and the frame-like substrate 40. However, the insulation layers are not shown in the figures.

The LED element 12 is disposed on the bottom surface 22 of the concave portion 23. The indicator layer 16 is disposed on an upper side of the LED element 12 on an inside of the concave portion 23. Note that, for example, a reflection layer 12A made of metal with high reflectivity is formed on a bottom surface and a side surface of the LED element 12. The LED element 12 generates the excitation light E only toward the indicator layer 16. The LED element 12 having the reflection layer 12A on the bottom surface irradiates the excitation light E, which has a light amount about twice as large as a light amount of an LED element without a reflection layer, toward the indicator layer 16. Irradiation of noise light due to the excitation light E on the indicator layer 16 can be prevented by the reflection layer 12A on the side surface. The same effect can be obtained when, instead of the reflection layer 12A, a PD element 13 is formed in a region of the side surface 24 of the concave portion 23 opposed to the side surface of the LED element 12.

The light-emitting element is not limited to the LED element 12 and is selected out of various kinds of light-emitting elements such as an organic EL element, an inorganic EL element, and a laser diode element. The LED element 12 is desirable from the viewpoints of, for example, fluorescent light transmittance, light generation efficiency, and broadness of wavelength selectivity of the excitation light E and that only a little light having wavelength other than an ultraviolet ray, which is the excitation light E, is generated.

The transparent resin layer 15 is a second protective layer. As the second protective layer, epoxy resin, silicone resin, transparent amorphous fluorocarbon resin, or the like can be used. The second protective layer is selected out of materials having characteristics that, for example, the materials have electric insulation, have moisture barrier properties, and have satisfactory transparency to the excitation light E and the fluorescent light F.

As the characteristics of the second protective layer, it is important that generation of the fluorescent light in the layer is small even if the excitation light E is irradiated. It goes without saying that the characteristic that the fluorescent light is small is an important characteristic of all transparent materials of the fluorescence sensor 10 excluding the indicator layer 16.

The indicator layer 16 generates, with the interaction with an analyte 9 penetrating into the indicator layer 16 and the excitation light E, the fluorescent light F having a light amount corresponding to the concentration of an analyte 9. Thickness of the indicator layer 16 is set to several tens of micrometers to about 200 μm. The indicator layer 16 is configured by a base material including a fluorescent pigment that generates the fluorescent light F having intensity corresponding to an amount of the analyte 9, i.e., analyte concentration in a specimen.

The fluorescent pigment is selected according to a type of the analyte 9. Any fluorescent pigment can be used as long as the light amount of the generated fluorescent light F reversibly changes according to the amount of the analyte 9. For example, when hydrogen ion concentration or carbon dioxide in a living organism is measured, a hydroxypyrene-tri sulfonic acid derivative, a phenylboronic acid derivative having a fluorescence residue when saccharides are measured, a crown ether derivative having a fluorescence residue when a potassium ion is measured, or the like can be used. When saccharides such as glucose are measured, as the fluorescent pigment, a ruthenium organic complex, a fluorescence phenylboronic acid derivative, or a substance reversibly coupled to glucose such as fluorescein coupled to protein can be used.

As explained above, the fluorescence sensor 10 according to the present invention is adapted to various uses such as an oxygen sensor, a glucose sensor, a pH sensor, an immunosensor, and a microbial sensor according to the selection of the fluorescent pigment.

The indicator layer 16 has, for example, an easily-hydrated hydrogel as a base material. In the hydrogel, the fluorescent pigment is contained or coupled. As a component of the hydrogel, a polysaccharide such as methylcellulose or dextran, acrylic hydrogel manufactured by polymerizing monomer such as (meta)acrylamide, methylol acrylamide, or hydroxyethyl acrylate, urethane hydrogel manufactured from polyethylene glycol and diisocyanate, or the like can be used.

The indicator layer 16 is bonded on the transparent resin layer 15 via a not-shown adhesive layer formed of a silane coupling agent or the like. Note that a structure in which the transparent resin layer 15 is not formed and the indicator layer 16 is directly bonded to the surface of the LED element 12 may be adopted.

The light blocking layer 19 is a layer having thickness equal to or smaller than several tens of micrometers formed on an upper surface side of the indicator layer 16. The light blocking layer 19 prevents the excitation light E and the fluorescent light F from leaking to an outside of the fluorescence sensor 10 and, at the same time, prevents external light from penetrating into the concave portion 23.

On the other hand, the photodiode (hereinafter also referred to as "PD") element 13, which is a photoelectric conversion element that receives the fluorescent light F and outputs a detection signal, is formed on the wall surface 45 of the through-hole 46 of the frame-like substrate 40, i.e., the side surface 24 of the concave portion 23 of the detection substrate section 20. That is, the PD element 13 is provided to surround the indicator layer 16 and formed such that a light receiving surface faces the indicator layer 16.

The PD element 13 may be formed over the entire side surface 24. However, in order to efficiently receive only the fluorescent light F, the PD element 13 may be formed only in an opposed region of the indicator layer 16. The indicator layer 16 may be formed on all four surfaces of the side surface 24 or may be formed in on a part of the four surfaces.

That is, the PD element 13 only has to be formed in at least a part of the side surface 24 of the concave portion 23.

As the photoelectric conversion element, a photoconductor, a phototransistor (PT), or the like may be used.

A silicon oxide layer 42, which is a first protective layer that protects the PD element 13, and a filter 41 are disposed to cover the PD element 13 formed on the side surface 24. The filter 41 is formed on a light-receiving surface side of the PD element 13 to cover the PD element 13.

The filter 41 is, for example, an absorption type filter that cuts the excitation light E without allowing the excitation light E to pass and allows the fluorescent light F having wavelength longer than the wavelength of the excitation light E to pass. As a material of such a filter, a silicon layer or a silicon carbide layer is suitable. The filter 41 may be a band-pass filter that allows only the fluorescent light F to pass.

The wiring substrate 30 includes two wires 61 and 62 for transmitting detection signals outputted from electrodes 43 and 44 of the PD element 13 to the main body section 2 and two wires 63 and 64 for transmitting a driving signal to an electrode 12B of the LED element. An N-type impurity, for example, phosphorus or arsenic is partially introduced to a surface of the frame-like substrate 40, which is an N-type semiconductor to form a low-resistance region 40H having higher electric conductivity. The electrode 44 is formed on the low-resistance region 40H.

The material of the frame-like substrate 40 is desirably monocrystal silicon in order to form the PD element 13 on the frame-like substrate 40. However, the material may be glass, ceramic, or the like.

It is desirable to prevent the fluorescent light F generated by the indicator layer 16 from leaking to an outside and block the external light to prevent the external light from penetrating into the concave portion 23. That is, it is desirable to coat, with a material same as the light blocking layer 19 or resin mixed with carbon black, the outer wall and the second principal plane 25 of the detection substrate section 20 or deposit a metal layer on the outer wall and the second principal plane 25.

The excitation light E generated by the LED element 12 is irradiated on the fluorescent pigment in the indicator layer 16. A part of the fluorescent light F generated by the fluorescent pigment through the interaction with the analyte 9 reaches the PD element 13 passing through the filter 41 and is converted into a detection signal.

The fluorescence sensor 10 has high detection sensitivity because the fluorescence sensor 10 detects the fluorescent light F with the PD element 13 formed on the side surface 24 that surrounds the indicator layer 16.

Next, a method of manufacturing the fluorescence sensor 10 is briefly explained. FIGS. 6A to 6E are partial sectional views of a region of one fluorescence sensor 10. However, in an actual process, a large number of elements are collectively formed in a wafer process.

Figure 6A:
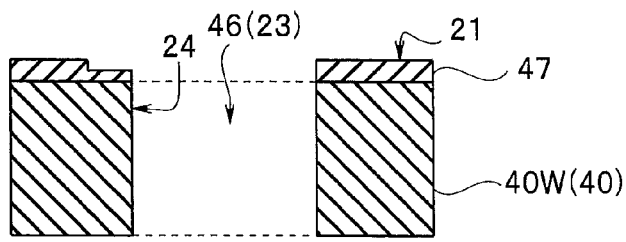
FIG. 6A is a schematic diagram showing a sectional structure for explaining a method of manufacturing a fluorescence sensor according to the first embodiment.

First, as shown in FIG. 6A, in manufacturing of the frame-like substrate 40, etching is applied to a conductive (N-type) first silicon wafer 40W via a mask layer 47. A large number of frame-like patterns, i.e., the through-hole 46 to be the concave portion 23 is formed. Publicly-known various methods can be used for the etching.

The size of an opening of the through-hole 46 is designed according to specifications. However, since a disposing place is the needle distal end portion 5, for example, an elongated shape having 150 µm longitudinally and 500 µm laterally is desirable.

In the fluorescence sensor 10, the side surface 24 of the concave portion 23 is perpendicular to the first principal plane 21. However, as explained below, the side surface may be a shape having a predetermined angle, i.e., tapered. A concave portion having a tapered shape can be manufactured by, for example, wet etching.

Figure 6B:
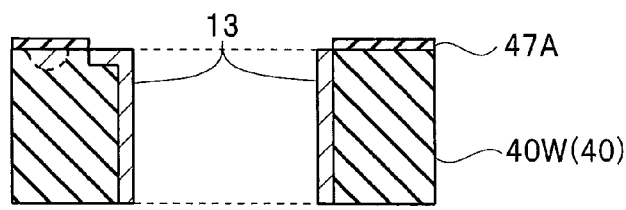
FIG. 6B is a schematic diagram showing a sectional structure for explaining the method of manufacturing a fluorescence sensor according to the first embodiment.

Subsequently, as shown in FIG. 6B, the PD element 13 is formed on the wall surface 45 of the through-hole 46 (the side surface 24 of the concave portion 23). That is, in a state in which the first silicon wafer 40W on which a mask layer 47A is formed is tilted at 5 degrees to 30 degrees, ion implantation processing is performed from four directions. For example, conditions under which boron (B) is introduced are an acceleration voltage of 10 to 100 keV and a dose amount of about $1 \times 10^{15}$ cm$^{-2}$. At this point, a thin oxide layer of 50 to 100 nm may be present on the first silicon wafer 40W.

The silicon oxide layer 42 and the filter 41 are formed in order by a CVD method to cover the PD element 13 on the wall surface 45 of the through-hole 46 of the first silicon wafer 40W. Further, the electrodes 43 and 44 are formed.

A conductive (N-type) second silicon wafer 30W to be the wiring substrate 30 is separately prepared. On the second silicon wafer 30W, the wires 61 and 62 for transmitting a detection signal from the PD element 13 and the wires 63 and 64 for supplying a driving signal to the LED element 12 are formed by a sputtering method, a vapor deposition method, or the like.

Figure 6C:
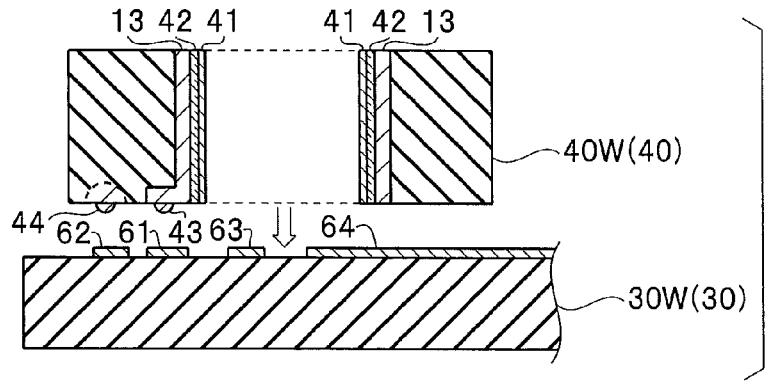
FIG. 6C is a schematic diagram showing a sectional structure for explaining the method of manufacturing a fluorescence sensor according to the first embodiment.

As shown in FIG. 6C, the first silicon wafer 40W is vertically reversed and bonded to the second silicon wafer 30W.

Figure 6D:
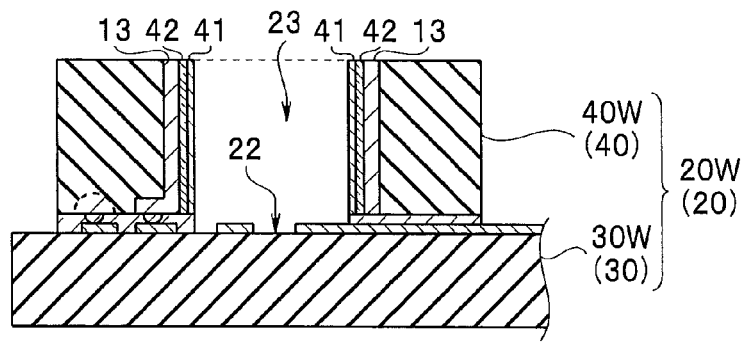
FIG. 6D is a schematic diagram showing a sectional structure for explaining the method of manufacturing a fluorescence sensor according to the first embodiment.

Then, as shown in FIG. 6D, in a bonded wafer 20W in which the two wafers are bonded, the through-hole 46 of the frame-like substrate 40 is the concave portion 23 having the bottom surface 22.

Figure 6E:
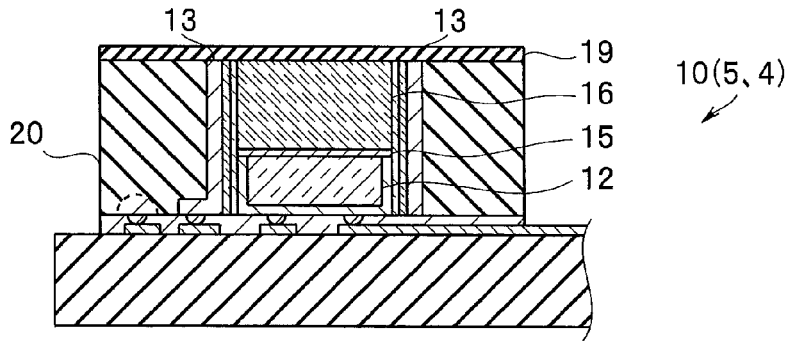
FIG. 6E is a schematic diagram showing a sectional structure for explaining the method of manufacturing a fluorescence sensor according to the first embodiment.

As shown in FIG. 6E, on an inside of each of a plurality of concave portions 23 of the bonded wafer 20W, the LED element 12 and the transparent resin layer 15 are disposed. Further, the indicator layer 16 is disposed on an upper side of the transparent resin layer 15, when necessary, via a bonding layer such as a silane coupling agent.

For the disposing of the LED element 12, methods including various bonding methods such as a bonding method in which optically transparent acrylic resin, silicon resin, or the like is used and a flip-chip bonding method can be used.

Finally, after the light blocking layer 19 is formed to cover the indicator layer 16, the bonded wafer 20W is singulated and the fluorescence sensor 10 is completed. That is, the needle-type fluorescence sensor 4 including the fluorescence sensor 10 at the needle distal end portion 5 is completed.

The method of manufacturing a fluorescence sensor is not limited to this. A method of, for example, after bonding the singulated wiring substrate 30 and the singulated frame-like substrate 40, disposing the LED element 12 and the like in the concave portion 23 may be used.

A first silicon wafer may be processed such that an extended portion of the wiring substrate 30 configures the needle main body portion 6 of the needle section 7. The needle main body portion 6 and the needle distal end portion 5 including the fluorescence sensor 10, which are separately manufactured, may be bonded to configure the needle section 7.

As explained above, the fluorescence sensor 10 according to the present embodiment can be collectively mass-produced by the wafer process. Therefore, the fluorescence sensor 10 can be provided inexpensively and with high quality.

Next, the operation of the fluorescence sensor 10 is explained with reference to FIG. 5.

The LED element 12 causes pulse light emission of the excitation light E having center wavelength of about 375 nm, for example, at an interval of once in thirty seconds. For example, a pulse current to the LED element 12 is 1 mA to 100 mA and pulse width of light emission is 10 ms to 100 ms.

The excitation light E generated by the LED element 12 enter the indicator layer 16 passing through the transparent resin layer 15. The indicator layer 16 emits the fluorescent light F of which intensity corresponds to an amount of the analyte 9. The analyte 9 penetrates into the indicator layer 16 passing through the light blocking layer 19. The fluorescent pigment of the indicator layer 16 generates the fluorescent light F with longer wavelength, for example, wavelength of 460 nm with respect to the excitation light E with wavelength of 375 nm.

A part of the fluorescent light F generated by the indicator layer 16 enter the PD element 13 through the filter 41 and the silicon oxide layer 42. The fluorescent light F is photoelectrically converted in the PD element 13 to generate photogenerated charges to be outputted as a detection signal. Note that a part of the excitation light E generated by the LED element 12 enter the side surface 24 of the concave portion 23. However, the excitation light E hardly enter the PD element 13 by the action of the filter 41.

In the fluorescence sensor 10, a computing section (not shown in the figure) of the main body section 2 performs computing processing on the basis of the detection signal, i.e., an electric current due to the photogenerated charges from the PD element 13 or a voltage due to accumulated photogenerated charges and calculates an analyte amount. Note that the needle-type fluorescence sensor 4 may include a computing section, a detection signal processing circuit, or the like.

The fluorescence sensor 10 includes the LED element 12 on the bottom surface 22 of the concave portion 23 of the detection substrate section and includes the PD element 13 on the side surface 24. Therefore, although the fluorescence sensor 10 is very small, detection sensitivity is high.

Modification of the First Embodiment

Next, a needle-type fluorescence sensor 4A including a fluorescence sensor 10A according to a modification of the first embodiment of the present invention is explained. The fluorescence sensor 10A according to this modification is similar to the fluorescence sensor 10 according to the first embodiment. Therefore, the same components are denoted by the same reference numerals and signs and explanation of the components is omitted.

As shown in FIG. 7A, the LED element 12 of the fluorescence sensor 10 according to the first embodiment includes a semiconductor 12N of a gallium nitride compound having thickness of about 10 μm formed on a sapphire substrate 12S having thickness of about 60 to 100 μm.

Therefore, for example, when thickness of the LED element 12 is 100 μm and depth of the concave portion is 150 μm, the thickness of the indicator layer 16 of the fluorescence sensor 10 is equal to or smaller than 50 μm.

On the other hand, as shown in FIG. 7B, in an LED element 12T of the fluorescence sensor 10A, most of the sapphire substrate 12S is removed from the LED element 12. The LED element 12T mainly includes the semiconductor 12N made of the gallium nitride compound. That is, thickness of the LED element 12T is about 10 μm. Note that a reflection layer 12A is formed on a side surface of the LED element 12T as well. However, since the thickness of the LED element 12T is small, the reflection layer 12AA may be formed only on a bottom surface of the LED element 12T.

In the fluorescence sensor 10A, for example, when the depth of the concave portion is 150 μm, thickness of the indicator layer 16A can be set to 140 μm thicker than the indicator layer 16 of the fluorescence sensor 10.

The fluorescence sensor 10A has the effect of the fluorescence sensor 10. Further, since the indicator layer 16A is thick, the fluorescence sensor 10A can generate a larger amount of the fluorescent light F. Therefore, the fluorescence sensor 10A has higher detection sensitivity.

Second Embodiment

Next, a needle-type fluorescence sensor 4B including a fluorescence sensor 10B according to a second embodiment of the present invention is explained. The fluorescence sensor 10B according to the present embodiment is similar to the fluorescence sensor 10 according to the first embodiment. Therefore, the same components are denoted by the same reference numerals and signs and explanation of the components is omitted.

As shown in FIG. 8, in the fluorescence sensor 10B, a PD element 13B, which is a second photoelectric conversion element, is formed on the bottom surface 22 of the concave portion 23 (an upper surface of a wiring substrate 30B) in addition to a PD element 13A, which is a first photoelectric conversion element, formed on a side surface 24 of the concave portion 23 of a detection substrate section 20B (the wall surface 45 of the through-hole 46 of the frame-like substrate 40).

A silicon oxide layer 42B, which is a third protective layer that protects the PD element 13B, and a filter 41B are disposed to cover the PD element 13B formed on the bottom surface 22. The silicon oxide layer 42B has a function same as the function of the silicon oxide layers 42 and 42A. The filter 41B has a function same as the function of the filters 41 and 41A. A reflection layer 12A1 of the LED element 12 is formed only on the side surface and is not formed on the bottom surface. The LED element 12 is a light-emitting element that transmits the fluorescent light F.

Respective center portions of the PD element 13B, the LED element 12, and the indicator layer 16 are formed in the same region on an upper side of the wiring substrate 30B.

In a manufacturing process for the fluorescence sensor 10B, a large number of PD elements 13B and the respective wires 60 (61 to 66) are formed on a surface of a second silicon wafer to be the wiring substrate 30B. The silicon oxide layer 42B of which thickness of several tens to several hundreds of nanometers to be a first protective layer is formed on a surface of the PD element 13B. Further, the filter 41B made of polycrystal silicon or the like is formed on a surface of the silicon oxide layer 42B.

Following steps are the same as the steps of the manufacturing process for the fluorescence sensor 10 explained above. Note that a detection signal of the PD element 13B is transmitted to the main body section 2 via the wires 65 and 66.

In the fluorescence sensor 10B, a part of the fluorescent light F generated by the indicator layer 16 reaches the PD element 13B passing through the LED element 12. Therefore, the PD element 13B generates a detection signal B. That is, the LED element 12 not including a reflection layer on the bottom surface transmits the fluorescent light F.

The fluorescence sensor 10B outputs, to the main body section 2, not only the detection signal A outputted by the PD element 13A but also the detection signal B outputted by the PD element 13B.

Therefore, the fluorescence sensor 10B has the effect of the fluorescence sensor 10 and has higher detection sensitivity.

Note that, when size of the LED element 12 is smaller than the PD element 13B, a reflection layer may be formed on the bottom surface of the LED element 12 either. In this case, since a part of the fluorescent light F is reflected by the reflection layer 12A, the part of the fluorescent light F does not enter the PD element 13B. However, a noise light component of a detection signal of the PD element 13B due to the excitation light E from the LED element 12 can be further reduced.

The PD element 13B does not have to be formed in a region opposed to the bottom surface of the LED element 12 in order to reduce the noise light component. That is, the PD element 13B only has to be formed in at least a part of the bottom surface 22 of the concave portion 23.

In the fluorescence sensor 10B according to the second embodiment as well, a thinned LED element same as the LED element 12T in the modification of the first embodiment may be used.

Modification of the Second Embodiment

Next, a needle-type fluorescence sensor 4C including a fluorescence sensor 10C according to a modification of the second embodiment of the present invention is explained. Since the fluorescence sensor 10C according to this modification is similar to the fluorescence sensor 10B according to the second embodiment, the same components are denoted by the same reference numerals and signs and explanation of the components is omitted.

The fluorescence sensor 10B according to the second embodiment outputs, to the main body section 2 respectively via the different wires 61, 62, 65, and 66, the detection signal A outputted by the PD element 13A and the detection signal B outputted by the PD element 13B.

On the other hand, the fluorescence sensor C outputs, to the main body section 2 using the two wires 67 and 68, an aggregated detection signal of the detection signal A outputted by the PD element 13A and the detection signal B outputted by the PD element 13B.

Figure 9:
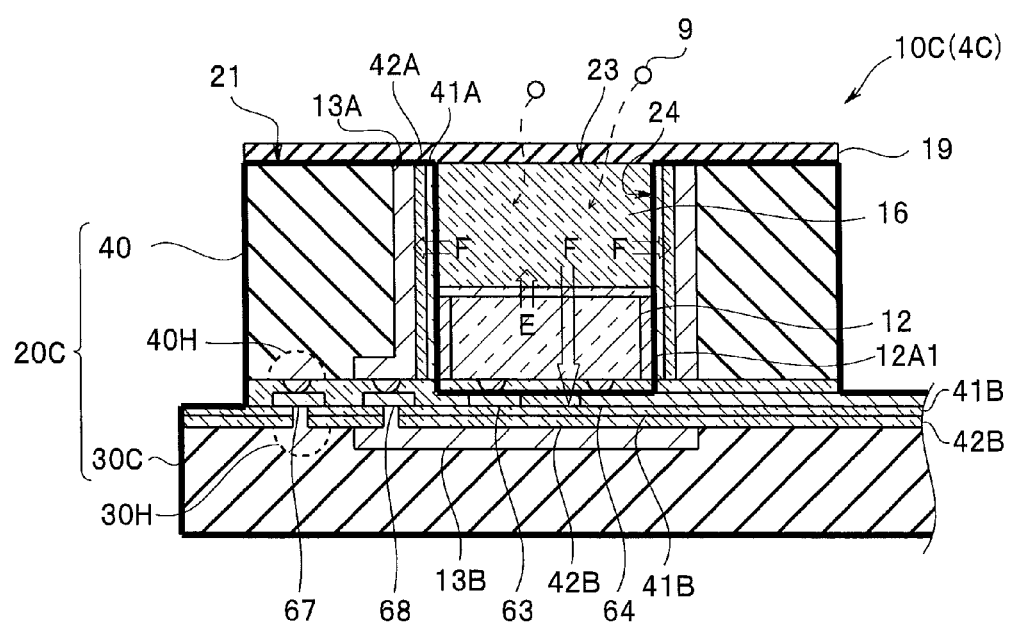
FIG. 9 is a schematic diagram showing a sectional structure of a fluorescence sensor according to a modification of the second embodiment.

That is, as shown in FIG. 9, a part of the PD element 13B formed on a wiring substrate 30C is extended to right under the frame-like substrate 40 and connected to the wire 68 of the PD element 13A right under the wire 68. A low-resistance region 30H of the wiring substrate 30C formed by a method same as the method of forming the low-resistance region 40H is connected to the common wire 67 right under the low-resistance region 40H of the frame-like substrate 40.

Electrical connection is performed using, for example, a flip-chip mounting technique or a solder connection technique.

The fluorescence sensor 10C has an effect of the fluorescence sensor 10B and the like. Further, since the number of the wires 60 for outputting a detection signal is as small as two, the fluorescence sensor 10C is smaller.

Third Embodiment

Next, a needle-type fluorescence sensor 4D including a fluorescence sensor 10D according to a third embodiment of the present invention is explained. The fluorescence sensor 10D according to this modification is similar to the fluorescence sensor 10 according to the first embodiment and the like, the same components are denoted by the same reference numerals and signs and explanation of the components is omitted.

A detection substrate section 20D of the fluorescence sensor 10D is integrally manufactured by a silicon wafer 20DW, which is a semiconductor substrate. That is, a concave portion 23D of the detection substrate section 20D is a concave portion formed on the first principal plane 21 of the silicon wafer 20DW by, for example, an etching method.

Next, a method of manufacturing the fluorescence sensor 10D is explained with reference to FIGS. 10A to 10E. FIGS. 10A to 10E are partial sectional views of a region of one fluorescence sensor 10D. However, in an actual process, a large number of elements are collectively formed in a wafer process.

Figure 10A:
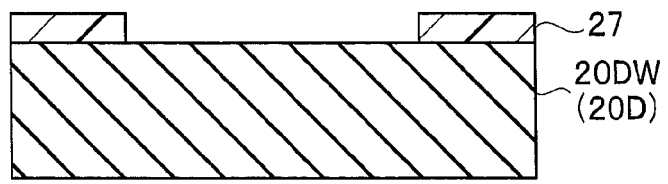
FIG. 10A is a schematic diagram showing a sectional structure for explaining a method of manufacturing a fluorescence sensor according to a third embodiment.
Figure 10B:
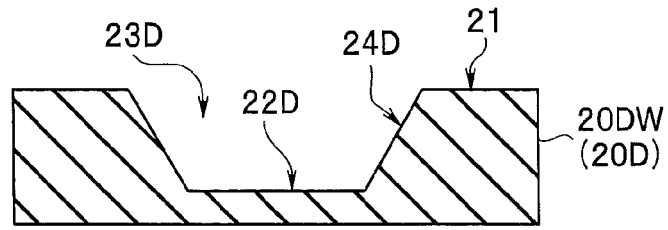
FIG. 10B is a schematic diagram showing a sectional structure for explaining the method of manufacturing a fluorescence sensor according to the third embodiment.

As shown in FIG. 10A, a mask layer 27 is manufactured on the first principal plane 21 of the silicon wafer 20DW. As shown in FIG. 10B, the concave portion 23D having a bottom surface 22D parallel to the first principal plane 21 is formed by the etching method.

As the etching method, a wet etching method in which a tetramethylammonium hydroxide (TMAH) solution, a potassium hydroxide (KOH) water solution, or the like is used is desirable. However, a dry etching method such as reactive ion etching (RIE), chemical dry etching (CDE), or the like can also be used.

For example, when silicon (100) surface is used as the silicon wafer 20DW, anisotropic etching is performed in which etching speed of a (111) surface is lower than etching speed of the (100) surface. Therefore, a side surface 24D of the concave portion 23D is the (111) surface and an angle θ1 between the (111) surface and the (100) surface is 54.74 degrees. That is, an opening of the concave portion 23D is wider than the bottom surface. The side surface 24D is formed in a tapered shape.

Figure 10C:
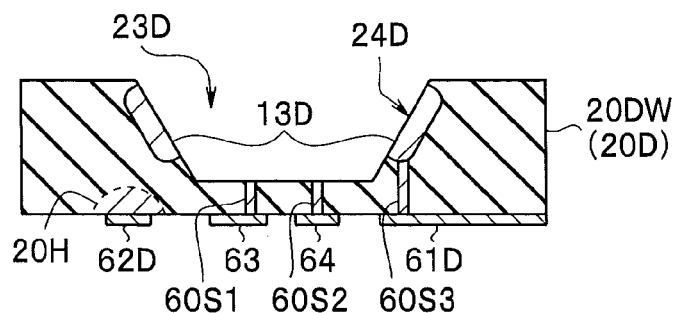
FIG. 10C is a schematic diagram showing a sectional structure for explaining the method of manufacturing a fluorescence sensor according to the third embodiment.

Subsequently, as shown in FIG. 10C, a PD element 13D is formed on the side surface 24D of the concave portion 23D. The concave portion 23D having the tapered side surface 24D has a large area in which the PD element is formed compared with the concave portion 23 having the vertical side surface 24. Moreover, it is easy to form the PD element 13D on the side surface 24D of the concave portion 23D.

Further, the wires 63 and 64 for a driving signal of a LED element 12D, wires 61D and 62D for a detection signal of the PD element 13D, and the like are formed. Note that through-wires 60S1, 60S2, and 60S3 for the LED element 12D and the PD element 13D may be manufactured before the formation of the PD element 13D. A low-resistance region 20H is formed by a method same as the method of forming the low-resistance region 40H.

Figure 10D:
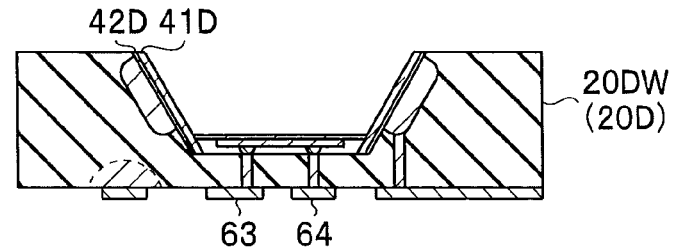
FIG. 10D is a schematic diagram showing a sectional structure for explaining the method of manufacturing a fluorescence sensor according to the third embodiment.

Subsequently, as shown in FIG. 10D, a silicon oxide layer 42D and a filter 41D are disposed to cover the PD element 13D on the side surface 24D. The silicon oxide layer 42D has a configuration and a function same as the configuration and the function of the silicon oxide layer 42. The filter 41D has a configuration and a function same as the configuration and the function of the filter 41.

Figure 10E:
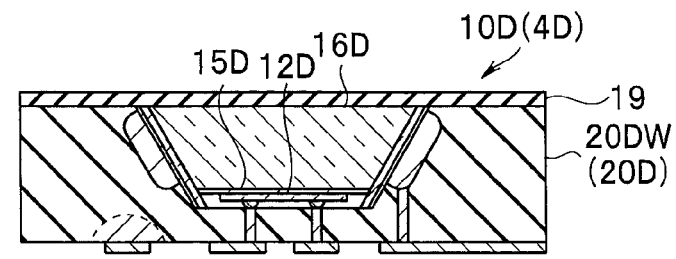
FIG. 10E is a schematic diagram showing a sectional structure for explaining the method of manufacturing a fluorescence sensor according to the third embodiment.

Subsequently, as shown in FIG. 10E, the LED element 12D including a reflection layer 12AD is disposed on the bottom surface 22D of the concave portion 23D. Further, an indicator layer 16D is disposed via a transparent resin layer 15D. Further, the silicon wafer 20DW on which a light blocking layer 19D is formed is singulated, whereby the fluorescence sensor 10D is completed.

Note that, depending on specifications of a fluorescence sensor, as in the fluorescence sensor 10, a side surface of a concave portion may be perpendicular to the first principal plane 21.

Note that the LED element 12D of the fluorescence sensor 10D according to the third embodiment is a thinned LED element same as the LED element 12T according to the modification of the first embodiment.

The fluorescence sensor 10D has an effect of the fluorescence sensor 10 and the like. Further, the fluorescence sensor 10D is easily manufactured and has higher sensitivity.

Modification of Third Embodiment

Next, a needle-type fluorescence sensor 4E including a fluorescence sensor 10E according to a modification of the third embodiment of the present invention is explained. The fluorescence sensor 10E according to this modification is similar to the fluorescence sensor 10D according to the third embodiment and the like. Therefore, the same components are denoted by the same reference numerals and signs and explanation of the components is omitted.

Figure 11:
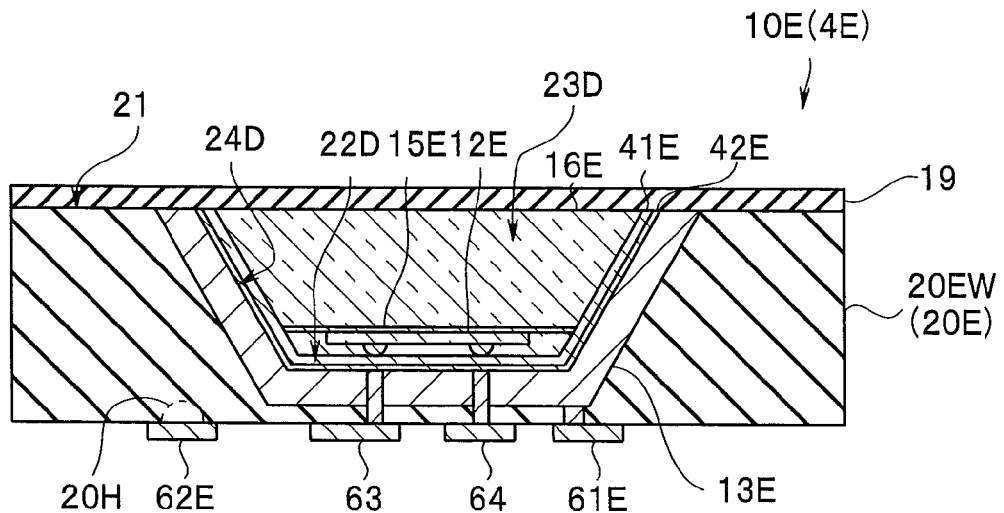
FIG. 11 is a schematic diagram showing a sectional structure of a fluorescence sensor according to a fourth embodiment.

As shown in FIG. 11, in the fluorescence sensor 10E, a PD element 13E, which is a photoelectric conversion element, is formed on the side surface 24D of the concave portion 23D of the detection substrate section 20E and the bottom surface 22D of the concave portion 23D.

In a manufacturing process for the fluorescence sensor 10E, the PD element 13E is formed simultaneously on the side surface 24D and the bottom surface 22D of the concave portion 23D of a silicon wafer 20EW on which the concave portion 23D having the bottom surface 22D parallel to the first principal plane 21 is formed. That is, a PD element formed on the side surface 24D and a PD element formed on the bottom surface are the integral PD element 13E.

Further, a silicon oxide layer 42E to be a first protective film of the PD element 13E is formed. A filter 41E made of polycrystal silicon or the like is formed on a surface of the silicon oxide layer 42E.

Following steps are the same as the steps of the method of manufacturing the fluorescence sensor 10D according to the third embodiment. However, an LED element 12E does not include a reflection layer on a bottom surface.

In the fluorescence sensor 10E according to the present embodiment, as in the fluorescence sensor 10B, the PD element 13E detects the fluorescent light F transmitted through the LED element 12E as well. Therefore, detection sensitivity is high.

Further, the PD element 13E integrally formed on the side surface 24D and the bottom surface 22D is easily formed. Moreover, wires for a detection signal only have to be two wires 61E and 62E. The silicon oxide layer 42E and the filter 41E can also be integrally formed on the side surface 24D and the bottom surface 22D.

The PD element 13D may be divided into a plurality of regions. Detection signals of the respective regions may be transmitted to the main body section 2 by separate wires.

The fluorescence sensor 10E has the effect of the fluorescence sensor 10D. Further, the fluorescence sensor 10E has high sensitivity and is easily manufactured.

Fourth Embodiment

Next, a needle-type fluorescence sensor 4F (4F1, 4F2) including a fluorescence sensor 10F (10F1, 10F2) according to a fourth embodiment of the present invention is explained. The fluorescence sensor 10F according to the present embodiment is similar to the fluorescence sensor 10 according to the first embodiment and the like. Therefore, the same components are denoted by the same reference numerals and signs and explanation of the components is omitted.

The fluorescence sensor 10F includes a long-wavelength cut filter 51 configured to cut long-wavelength light including excitation light having high transmittance in a wavelength range of the fluorescent light F and having low transmittance in a wavelength range longer than the wavelength range of the fluorescent light F among lights generated by the LED element 12.

As explained above, the LED element 12 generates the excitation light E having center frequency of, for example, about 375 nm. However, the excitation light E sometimes includes a slight amount of light having wavelength longer than the wavelength of the fluorescent light F. That is, because of an influence of a crystal defect inherent in a crystal forming the LED element 12, in some case, faint emitted light appears from the LED element 12 in a wavelength range wide on a long wavelength side. Further, reception sensitivity of the PD element 13 is high on the long wavelength side. Transmittance of the filter is also high on the long wavelength side.

Therefore, a wavelength component spectrum longer than the wavelength of the fluorescent light F of the LED element 12 does not contribute to fluorescent light generation of the indicator layer 16. Moreover, even if the wavelength component spectrum is weak, the wavelength component spectrum is a significant cause of a noise component of a detection signal.

Figure 12:
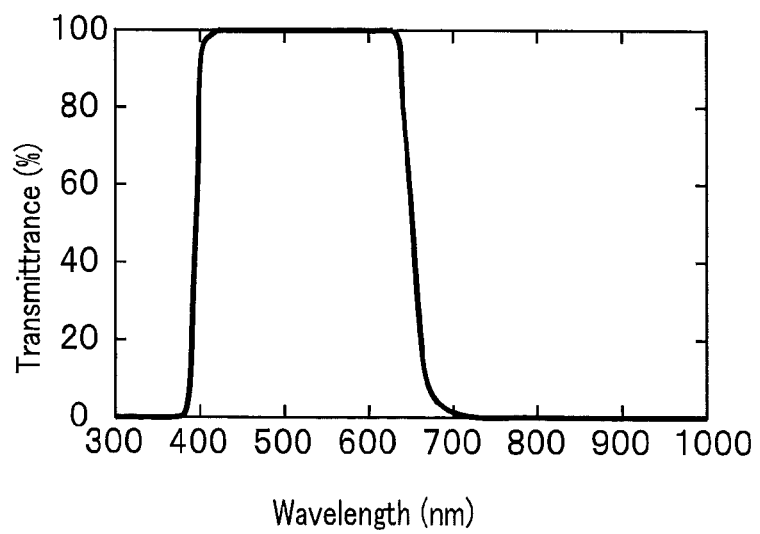
FIG. 12 is a diagram showing a characteristic of a long wavelength cut filter of a fluorescence sensor according to a fifth embodiment.

In FIG. 12, an example of a transmittance characteristic of a long-wavelength cut filter 51 suitable for detection of the florescent light F with peak wavelength of 475 nm, a short wavelength end of 425 nm, and a long wavelength end of 650 nm is shown. The long-wavelength cut filter 51 is transparent in a wavelength range of the fluorescent light F.

The long-wavelength cut filter 51 is a dielectric multilayer film manufactured by laminating multiple layers of dielectrics such as $LaF_3$, $Al_2O_3$, $Pr_2O_3$, $Ta_2O_3$, $TiO_2$, or $Nb_2O_5$.

Figure 13A:
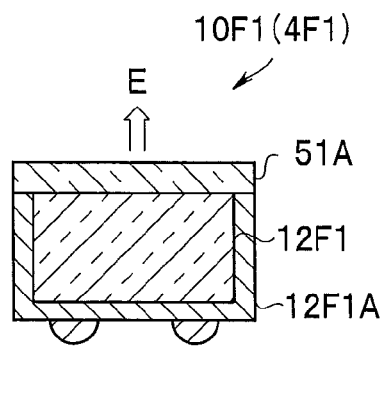
FIG. 13A is a schematic diagram showing a sectional structure of the fluorescence sensor according to the fifth embodiment.
Figure 13B:
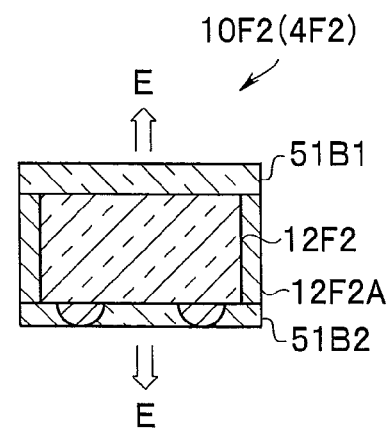
FIG. 13B is a schematic diagram showing a sectional structure of the fluorescence sensor according to the fifth embodiment.

As shown in FIG. 13A, in the fluorescence sensor 10F1 in which an LED element 12F1 emits the excitation light E only upward, a long-wavelength cut filter 51A is disposed above the LED element 12F1 including a reflection layer 12F1A. As shown in FIG. 13B, in the fluorescence sensor 10F2 in which an LED element 12F2 including a reflection layer 12F2A emits the excitation light E upward and downward, long-wavelength cut filters 51B1 and 51B2 are dispose above and below the LED element 12.

As shown in FIG. 13A, in the fluorescence sensor 10F1 in which an LED element 12F1 emits the excitation light E only upward, a long-wavelength cut filter 51A is disposed above the LED element 12F1 including a reflection layer 12F1A. As shown in FIG. 13B, in the fluorescence sensor 10F2 in which an LED element 12F2 including a reflection layer 12F2A emits the excitation light E upward and downward, long-wavelength cut filters 51B1 and 51B2 are dispose above and below the LED element 12F2.

In the fluorescence sensor 10F according to the present embodiment, since long-wavelength light generated by the LED element 12 is cut by the long-wavelength cut filter 51, noise light to be an offset output is removed. Therefore, S/N of a detection signal is improved. Consequently, the fluorescence sensor 10F has the effect of the fluorescence sensor 10 or the like and has higher sensitivity.

The present invention is not limited to the embodiments and the modifications explained above and combinations, various alterations, modifications, and the like of the embodiments and the modifications can be made without departing from the spirit of the invention.

What is claimed is:

1. A fluorescence sensor comprising:
a detection substrate section, on a first principal plane of which a concave portion having a bottom surface parallel to the first principal plane is present and, in at least a part of a side surface of the concave portion of which a photoelectric conversion element configured to receive fluorescent light and output a detection signal is formed;
a light-emitting element disposed on the bottom surface of the concave portion of the detection substrate section and configured to generate excitation light; and
an indicator layer disposed on an inside of the concave portion on an upper side of the light-emitting element and configured to generate the fluorescent light corresponding to the excitation light and an analyte amount.

2. The fluorescence sensor according to claim 1, wherein the detection substrate section includes a wiring substrate and a frame-like substrate bonded to the wiring substrate, the frame-like substrate forming a through-hole to be the concave portion, and
a surface of the wiring substrate is the bottom surface of the concave portion, and a wall surface of the through-hole in the frame-like substrate is the side surface of the concave portion.

3. The fluorescence sensor according to claim 2, wherein a filter configured to transmit the fluorescent light and cut the excitation light is formed to cover a light-receiving surface of the photoelectric conversion element.

4. The fluorescence sensor according to claim 3, further comprising a long-wavelength cut filter configured to cut a long-wavelength component of the excitation light generated by the light-emitting element.

5. The fluorescence sensor according to claim 4, wherein the fluorescence sensor is a needle-type sensor including a connector section configured to fit with a fitting section of a main body section arranged outside of a body, the needle-type sensor measuring an analyte in the body.

6. The fluorescence sensor according to claim 3, wherein a second photoelectric conversion element configured to receive the fluorescent light and output a second detection signal is formed in at least a part of the bottom surface of the concave portion.

7. The fluorescence sensor according to claim 6, wherein respective center portions of the second photoelectric conversion element, the light-emitting element, and the indicator layer are formed in a same region in the concave portion.

8. The fluorescence sensor according to claim 7, further comprising a wire configured to output an aggregated detection signal of the detection signal of the photoelectric conversion element and the second detection signal of the second photoelectric conversion element.

9. The fluorescence sensor according to claim 1, wherein the concave portion is a concave portion formed in the detection substrate section composed of a semiconductor substrate.

10. The fluorescence sensor according to claim 9, wherein an opening of the concave portion is wider than the bottom surface, and the side surface is formed in a tapered shape.

11. The fluorescence sensor according to claim 10, wherein a filter configured to transmit the fluorescent light and cut the excitation light is formed to cover a light-receiving surface of the photoelectric conversion element.

12. The fluorescence sensor according to claim 11, further comprising a long-wavelength cut filter configured to cut a long-wavelength component of the excitation light generated by the light-emitting element.

13. The fluorescence sensor according to claim 12, wherein the fluorescence sensor is a needle-type sensor including a connector section configured to fit with a fitting section of a main body section arranged outside of a body, the needle-type sensor measuring an analyte in the body.

14. The fluorescence sensor according to claim 11, wherein a second photoelectric conversion element configured to receive the fluorescent light and output a second detection signal is formed in at least a part of the bottom surface of the concave portion.

15. The fluorescence sensor according to claim 14, wherein the photoelectric conversion element and the second photoelectric conversion element are simultaneously integrally formed on the side surface and the bottom surface of the concave portion.

16. The fluorescence sensor according to claim 15, wherein respective center portions of the second photoelectric conversion element, the light-emitting element, and the indicator layer are formed in a same region in the concave portion.

17. The fluorescence sensor according to claim 14, further comprising a wire configured to output an aggregated detection signal of the detection signal of the photoelectric conversion element and the second detection signal of the second photoelectric conversion element.

* * * * *